US008416643B2

(12) United States Patent
Magee

(10) Patent No.: US 8,416,643 B2
(45) Date of Patent: Apr. 9, 2013

(54) RECEIVE BEAMFORMER FOR ULTRASOUND HAVING DELAY VALUE SORTING

(75) Inventor: David Patrick Magee, Allen, TX (US)

(73) Assignee: Texas Instruments Incorporated, Dallas, TX (US)

(*) Notice: Subject to any disclaimer, the term of this patent is extended or adjusted under 35 U.S.C. 154(b) by 426 days.

(21) Appl. No.: 12/726,514

(22) Filed: Mar. 18, 2010

(65) Prior Publication Data

US 2010/0249596 A1 Sep. 30, 2010

Related U.S. Application Data

(60) Provisional application No. 61/162,829, filed on Mar. 24, 2009.

(51) Int. Cl.
*H04B 1/02* (2006.01)
*A61B 8/00* (2006.01)

(52) U.S. Cl. ........................................ 367/138; 600/447

(58) Field of Classification Search .................. 367/138; 600/447

See application file for complete search history.

(56) References Cited

U.S. PATENT DOCUMENTS

| | | | | | |
|---|---|---|---|---|---|
| 5,469,851 | A | * | 11/1995 | Lipschutz | 600/447 |
| 5,477,859 | A | * | 12/1995 | Engeler | 600/447 |
| 5,544,128 | A | * | 8/1996 | Kim et al. | 367/119 |
| 5,647,365 | A | * | 7/1997 | Abboud | 600/447 |
| 5,827,188 | A | * | 10/1998 | Wright et al. | 600/447 |
| 5,856,955 | A | * | 1/1999 | Cole et al. | 367/138 |
| 5,995,450 | A | * | 11/1999 | Cole et al. | 367/138 |
| 6,042,547 | A | * | 3/2000 | Wright et al. | 600/447 |
| 6,104,673 | A | * | 8/2000 | Cole et al. | 367/138 |
| 6,110,116 | A | * | 8/2000 | Wright et al. | 600/447 |
| 6,135,961 | A | | 10/2000 | Pflugrath et al. | |
| 6,172,939 | B1 | * | 1/2001 | Cole et al. | 367/138 |
| 6,363,033 | B1 | * | 3/2002 | Cole et al. | 367/138 |
| 6,648,826 | B2 | | 11/2003 | Little et al. | |
| 7,604,596 | B2 | | 10/2009 | Hwang et al. | |
| 2002/0082500 | A1 | * | 6/2002 | Henderson et al. | 600/443 |
| 2003/0076904 | A1 | * | 4/2003 | Magee | 375/340 |
| 2003/0163047 | A1 | | 8/2003 | Little et al. | |
| 2004/0133110 | A1 | | 7/2004 | Little et al. | |
| 2005/0265267 | A1 | | 12/2005 | Hwang | |
| 2007/0055151 | A1 | * | 3/2007 | Shertukde et al. | 600/437 |
| 2009/0326375 | A1 | | 12/2009 | Magee | |
| 2010/0012119 | A1 | | 1/2010 | Sallak et al. | |

* cited by examiner

*Primary Examiner* — Isam Alsomiri
*Assistant Examiner* — James Hulka
(74) *Attorney, Agent, or Firm* — Alan A. R. Cooper; Wade J. Brady, III; Frederick J. Telecky, Jr.

(57) ABSTRACT

A method of processing ultrasound signals received from a plurality of data channels each associated with a transducer element. A sorted delay data table having sorted delay data is generated that includes a channel identifier, a fractional delay value, and integer delay value. The sorted delay data table clusters together channel groups including a first channel group having data channels with the first fractional delay value and a second channel group with data channels with the second fractional delay value. Control signals are generated based on the sorted delay data that implements data path combining by directing channel data from the first channel group for processing by a first interpolation filter that provides the first fractional delay value and channel data associated with the second channel group for processing by a second interpolation filter that provides the second fractional delay value. Summing signals output by the first and second interpolation filter forms the ultrasound beamformed signal.

10 Claims, 6 Drawing Sheets

| CHANNEL NUMBER (m) | FRAC DELAY | INT DELAY | UNSORTED TABLE HEX VALUE | SORTED TABLE HEX VALUE | |
|---|---|---|---|---|---|
| 0 | 3 | 4 | 0x00030004 | 0x00030004 | FRAC DELAY=0 |
| 1 | 2 | 4 | 0x00020004 | 0x00070003 | |
| 2 | 1 | 4 | 0x00010004 | 0x00080003 | |
| 3 | 0 | 4 | 0x00000004 | 0x800C0004 | |
| 4 | 3 | 3 | 0x00030003 | 0x01020004 | FRAC DELAY=1 |
| 5 | 2 | 3 | 0x00020003 | 0x01060003 | |
| 6 | 1 | 3 | 0x00010003 | 0x01090003 | |
| 7 | 0 | 3 | 0x00000003 | 0x810D0004 | |
| 8 | 0 | 3 | 0x00000003 | 0x02010004 | FRAC DELAY=2 |
| 9 | 1 | 3 | 0x00010003 | 0x02050003 | |
| 10 | 2 | 3 | 0x00020003 | 0x020A0003 | |
| 11 | 3 | 3 | 0x00030003 | 0x820E0004 | |
| 12 | 0 | 4 | 0x00000004 | 0x03000004 | FRAC DELAY=3 |
| 13 | 1 | 4 | 0x00010004 | 0x03040003 | |
| 14 | 2 | 4 | 0x00020004 | 0x030B0003 | |
| 15 | 3 | 4 | 0x00030004 | 0x830F0004 | |

*FIG. 3C*

RECEIVE BEAMFORMER FOR ULTRASOUND HAVING DELAY VALUE SORTING

CROSS REFERENCE TO RELATED APPLICATIONS

This application claims the benefit of Provisional Application Ser. No. 61/162,829 entitled "Method of Sorting Delay Values to Improve DSP Beamformer Performance" filed Mar. 24, 2009, which is herein incorporated by reference in its entirety.

FIELD OF THE INVENTION

Embodiments of the invention relate to receive beamformers for ultrasound and related beamforming algorithms, and integrated circuits (ICs) and ultrasound systems therefrom.

BACKGROUND

Beamforming is a signal processing technique used in sensor arrays for directional signal transmission or reception. Spatial selectivity is achieved by using adaptive or fixed receive/transmit beam patterns.

Beamforming can be used for both electromagnetic waves (e.g., RF) and sound waves, and has found a variety of applications in radar, seismology, sonar, wireless communications, radio astronomy, speech, and medicine. Adaptive beamforming is used to detect and estimate the signal-of-interest at the output of a sensor array using data-adaptive spatial filtering and interference rejection.

One medical application that uses beamforming is for ultrasound diagnostics. Ultrasound energy is focused at target tissue by a transmit beamformer, and ultrasound energy modulated and returned by the target tissue is focused by a receive beamformer. The receive beamformer may provide signals for generation of B-mode images, color Doppler or spectral Doppler information representing the target tissue, or combinations thereof. Such beamforming systems can provide real-time, cross-sectional (tomographic) 2D images of human body tissue or the tissue of another subject.

FIG. 1 shows a simplified block diagram depiction of a conventional delay and sum ultrasound receive beamformer system 100 for imaging target tissue 105. Beamformer system 100 comprises a plurality (M) of transducer elements 112 shown as eight transducer elements 112$_1$-112$_8$ which each comprise separate piezoelectric transducers that convert sound waves echoed by the target tissue 105 into electrical signals in the receive mode. Although only eight (M=8) transducer elements 112$_1$-112$_8$ are shown in FIG. 1, a practical ultrasound receive beamformer system 100 may have many more transducer elements, such as several hundred or more. Separate data processing paths 115$_1$-115$_8$ referred to herein as data channels are seen to be dedicated to each of the transducer elements 112$_1$-112$_8$.

The data processing paths 115$_1$-115$_8$ each comprise in serial connection a voltage controlled amplifier (VCA) 116, an analog to digital converter (ADC) 117 for digital conversion of the amplified transducer signal, and an integer delay 118 for adding the integer portion of the desired delay value. A plurality of interpolation filter banks 119 each comprising a plurality of interpolation filters (P) is also provided. The plurality of interpolation filters (P) in each interpolation filter bank 119$_1$-119$_8$ collectively provide a plurality of different fractional portions of the desired delay value for each of the data channels 115$_1$-115$_8$, since as known in the art the desired delay values are not integer multiples of the ADC sampling period (Ts) because in general the desired timing resolution (Tres) is <Ts.

For conventional ultrasound applications, Tres is generally between 1 to 10 nsec and the Ts of the ADCs 117 is generally from 20 to 200 nsec (corresponding to 50 MHz to 5 MHz operation). Tres thus determines the number of interpolation filters (P) in each interpolation filter bank 119$_1$-119$_8$ needed to provide the plurality of different fractional delay portions for each of the dedicated data channels 115$_1$-115$_8$ for beamformer system 100. For example, without decimation filtering, P=ceil(Ts/Tres) to achieve the desired Tres, such as P=20 interpolation filters in each interpolation filter bank 119$_1$-119$_8$ in the case Ts=20 nsec and Tres=1 nsec. The ceil function returns an integer by rounding its argument towards infinity (upward). Beamformer system 100 thus includes M interpolation filter banks 119, each containing P interpolation filters.

Several methods are known for interpolation filtering, such as Lagrangian, and sinc approximation. The implementation generally assumes a given number of finite impulse response (FIR) filter coefficients. It is usually assumed that the FIR filter coefficients can change on a sample-by-sample-basis. A polyphase interpolation FIR filter is a common implementation that reduces the number of computations required per cycle as compared to a direct implementation of an interpolation filter.

Each of the dedicated data channels 115$_1$-115$_8$ also include an apodization gain block 120 so that each received signal is scaled by a desired value by an apodization factor to reduce the grating side lobe effects in the later formed beamformed signal due to lateral pressure field amplitude variations and the spacing of the transducer elements 112$_1$-112$_8$. Apodization factors can generally be changed on a sample-by-sample basis. An adder 121 sums the respective signals from each of the data channels 115$_1$-115$_8$ provided by the respective apodization gain blocks 120$_1$-120$_8$ to generate the desired beamformed signal which can then be used to form an image of the target tissue 105 on a suitable display device.

The conventional delay and sum ultrasound receive beamformer system 100 described above produces effective focal points along a given scanline (e.g., such as the scanline shown in FIG. 1) to focus the receive echoes from portions of target tissue 105 that lie along a given scanline. When the receive beamformer system 100 beamforms more than one scanline, the beamforming is commonly referred to as Multiple Line Acquisition (MLA) for a given transmit pulse sequence.

In a conventional beamforming implementation, such as when using conventional delay and sum ultrasound receive beamformer system 100, the filtered signal response from each of the respective interpolation filter banks 119$_1$-119$_8$ from the received signal originating from its associated single associated transducer element 112 can be written as a summation over the filter coefficients k of the interpolation filters in the interpolation filter bank 119 as:

$$y_i[n] = \sum_{k=-\infty}^{\infty} h_{i(n)}[k]x_i[n-k-d_i[n]] \text{ for } 0 \le n \le N-1 \qquad \text{Equation \#1}$$

Where:

$x_i[n]$ is the signal from the $i^{th}$ receive data channels 115$_1$-115$_8$ at time sample n.

$h_{i(n)}[k]$ is the $k^{th}$ coefficient of the respective interpolation filter for the $i^{th}$ receive channel at time sample n.

$y_i[n]$ is the filtered signal for the $i^{th}$ receive data channels $115_1$-$115_8$ at time sample n.

$d_i[n]$ is the integer delay for $i^{th}$ receive data channels $115_1$-$115_8$ at time sample n.

It is noted that this filtering operation is piece-wise linear, i.e. at each sample instance n, the output of interpolation filter bank 119 is a linear combination of input samples. The beamformed signal response for a single scanline is found by summing (e.g., using summer 121) the responses from each of the data channels $115_1$-$115_8$ after processing by apodization gain blocks 120 to represent signals from all M receive transducer elements $112_1$-$112_8$, which can be expressed as:

$$z[n] = \sum_{m=0}^{M-1} a_m[n] \sum_{k=-\infty}^{\infty} h_{m(n)}[k] x_m[n - k - d_m[n]] \quad \text{Equation \#2}$$

Where $a_m[n]$ is the apodization factor for the $m^{th}$ receive signal at time sample n, and z[n] is the beamformed received signal at time sample n.

A measure of computational complexity for receive beamformers can be found by calculating the number of multiplies (referred to herein as numMults) needed for implementing the beamforming operation. To calculate z[n] as shown above, numMults is given by Equation 3 shown below:

$$\text{numMults} = L \cdot M \cdot (K+1) \cdot N \quad \text{Equation \#3}$$

Where K is the number of filter coefficients per interpolation filter, L is the number of MLAs, M is the number of receive transducer elements and N is the number of output samples. The numMults required in a beamformer algorithm determines the gate count in an IC implementation, and as a result the power dissipation and thus the cooling requirements for a given implementation. Due to the high numMults required for implementing the algorithm used by conventional beamformer data architecture, such as implemented by the delay and sum ultrasound receive beamformer system 100 shown in FIG. 1, such conventional beamformers have generally been limited to ASIC implementations and have had to significantly limit the number of data channels and thus the spatial resolution provided.

SUMMARY

Disclosed embodiments describe new control signal generating data architecture and delay value sorting methods for data path combined ultrasound receive beamformer systems. Commonly owned Pub. U.S. Application No. 2009/0326375 to Magee (hereafter Magee '375) discloses a data path combined ultrasound receive beamformer that implements data path combining before interpolation filtering, rather than data path combining after interpolation filtering used in conventional beamformer architectures. The Magee '375 disclosed beamformer architecture coupled with appropriate control signals allows channel data from any of the data channels in the system to be processed by any of the interpolation filters in a shared interpolation filter bank, and thus has less interpolation filters as compared to data channels which provides significantly higher computationally efficiency as compared to conventional data architectures for ultrasound receive beamforming. Magee '375 is incorporated herein by reference in its entirety.

Disclosed embodiments provide significant additional computational efficiency for the data path combined receive beamformer disclosed in Magee '375 by sorting channel data based on its fractional delay value into channel groups, and generating control signals therefrom that direct groups of data channels that have channel data with the same fractional delay to respective interpolation filters in the shared interpolation filter bank. Sorting channel data into channel groups based on fractional delay has been found by the Inventor to significantly reduce the cycle count per block of beamformed data which allows more blocks of beamformed data to be processed per computing device (e.g. DSP, FPGA or ASIC), and more scanlines to be processed per computing device.

Disclosed embodiments are generally described as being directed to receive beamforming for ultrasound applications. However, embodiments of the invention can also be used for electromagnetic (e.g., RF) applications, and other sound wave processing applications.

BRIEF DESCRIPTION OF THE DRAWINGS

FIG. 3C is an exemplary delay data table that shows table data at a particular sample time for channel data provided by a 16 channel receive beamformer system, an unsorted delay data table format based on the channel data format shown in FIG. 3A, and its re-mapping to a sorted delay data table format based on the channel data format shown in FIG. 3B.

DETAILED DESCRIPTION

Figure 1:
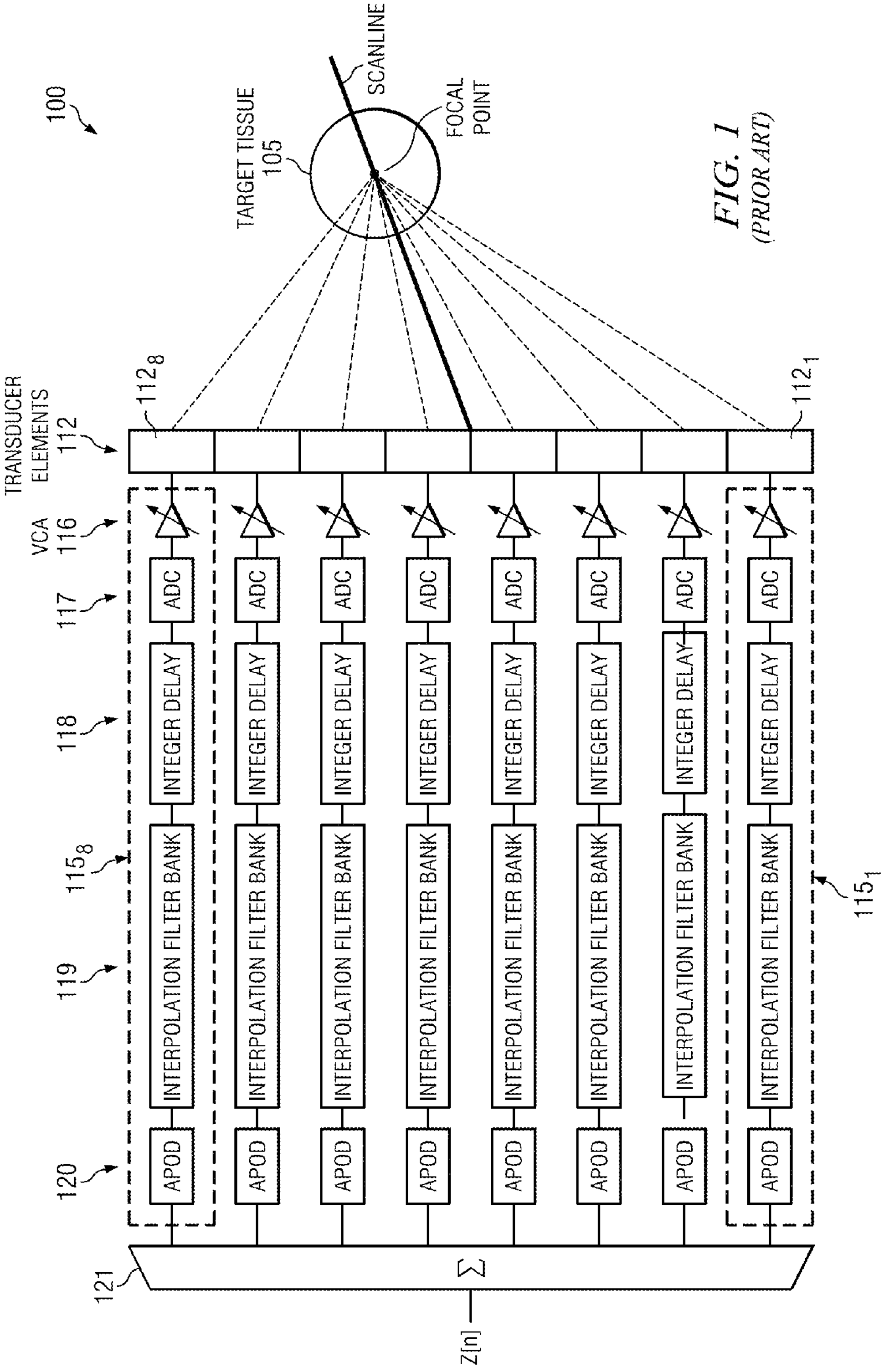
FIG. 1 (PRIOR ART)
FIG. 1 is a simplified block diagram depiction of a conventional delay and sum ultrasound receive beamformer system for imaging target tissue.

Disclosed embodiments are described with reference to the attached figures, wherein like reference numerals are used throughout the figures to designate similar or equivalent elements. The figures are not drawn to scale and they are provided merely to illustrate disclosed features. Several disclosed aspects are described below with reference to example applications for illustration. It should be understood that numerous specific details, relationships, and methods are set forth to provide a full understanding of this Disclosure. One having ordinary skill in the relevant art, however, will readily recognize that the subject matter in this Disclosure can be practiced without one or more of the specific details or with other methods. In other instances, well-known structures or operations are not shown in detail to avoid obscuring certain features. Disclosed embodiments of the invention are not limited by the illustrated ordering of acts or events, as some acts may occur in different orders and/or concurrently with other acts or events. Furthermore, not all illustrated acts or events are required to implement a methodology in accordance with this Disclosure.

Mathematically, the data path combined receive beamformers disclosed in Magee '375 invert (i.e., swap) the summations over m and k in Equation #2 shown above. Equation #2 sums first over k (interpolation filter coefficients) then over m (transducer elements). In contrast, Equation #4 shown below first sums over m (transducer elements), then over k (interpolation filter coefficients):

$$z[n] = \sum_{k=-\infty}^{\infty} \sum_{m=0}^{M-1} a_m[n] h_{m(n)}[k] x_m[n-k-d_m[n]] \qquad \text{Equation \#4}$$

Equation #4 can be rewritten as Equation #5 below which provides a mapping for the $m^{th}$ receive signal (corresponding to the $m^{th}$ data channel) to the $p^{th}$ interpolation filter in the shared interpolation filter bank:

$$z[n] = \sum_{k=-\infty}^{\infty} \sum_{m=0}^{M-1} a_m[n] h_{p(m,n)}[k] x_m[n-k-d_m[n]] \qquad \text{Equation \#5}$$

Where:

$p(m,n) \in \{0, 1, \ldots, P-1\}$ $P = \text{ceil}(T_s/T_{res})$

The control signal p(m,n) thus controls the selection of a particular one of the P interpolation filters in the shared interpolation filter bank provided by the beamformer system for processing sensing signal data originating from any of the M data channels at each time sample n. In the specific instance there are P=10 interpolation filters (e.g., when Ts=10*Tres) in the beamformer system, the respective interpolation filters in the shared interpolation filter bank can be embodied as interpolation filters each providing a different fractional delay h, such as filter $h_o$ (delay=0*$T_s$=0 (no delay)), $h_1$ (delay=1*$T_s$), $h_9$ (delay=9*$T_s$). z[n] in Equation #5 can be rewritten as Equation #6 shown below so that it provides mapping for the $p^{th}$ group of received signals back to the original $m^{th}$ received signal (corresponding to the $m^{th}$ data channel).

$$z[n] = \sum_{k=-\infty}^{\infty} \sum_{p=0}^{P-1} h_p[k] \sum_{s=0}^{S(p,n)-1} a_{I(p,s)}[n] x_{I(p,s)}[n-k-d_{I(p,s)}[n]] \qquad \text{Equation \#6}$$

Where I(p,s) provides a mapping for the $s^{th}$ signal in the $p^{th}$ group of received signals to the original $m^{th}$ received signal and S(p,n) is the number of receive signals using the $p^{th}$ interpolation filter in the shared interpolation filter bank at time sample n.

Equation #6 can be written as Equation #7:

$$z[n] = \sum_{k=-\infty}^{\infty} \sum_{p=0}^{P-1} h_p[k] z_p[n, k, d] \qquad \text{Equation \#7}$$

Where $$z_p[n, k, d] = \sum_{s=0}^{S(p,n)-1} a_{I(p,s)}[n] x_{I(p,s)}[n-k-d_{I(p,s)}[n]]$$

The total number of multiplies (numMults) in Equation #7 can be written as:

$$\text{numMults} = (M + L \cdot P) \cdot K \cdot N$$

Where K is the number of filter coefficients per interpolation filter, L is the number of MLAs; M is the number of receive transducer elements (i.e., equal to the number of data channels), N is the number of output samples, and P is the number of interpolation filters in the shared interpolation filter bank.

As described above in the Background (Equation 3), the numMults for the conventional ultrasound receive beamforming algorithm is:

$$\text{numMults} = L \cdot M \cdot (K+1) \cdot N$$

Accordingly, the ratio (Ratio) of numMults for the conventional ultrasound receive beamforming algorithm to ultrasound receive beamforming algorithms according to the data path combined receive beamformer disclosed in Magee '375 can be approximated by the following equation:

$$\text{Ratio} \approx 1/L + P/M.$$

Thus, as the Ratio decreases, the relative performance in terms of reducing numMults improves. The relative performance of the data path combined receive beamformer disclosed in Magee '375 can be seen to improve as the number of transducer elements (M)/data channels increases, which is known to improve spatial resolution, and decreases as the total number of interpolation filters increases. As described above, the minimum number of interpolation filters can be set by Ts and Tres by P=ceil(Ts/Tres). Since M>>P in practical ultrasound beamforming systems, the data path combined receive beamformer disclosed in Magee '375 generally significantly reduces numMults.

As noted above, disclosed embodiments describe new control signal generating data architecture and delay value sorting for imaging target tissue for data path combined receive beamforming applications. As described above, such embodiments provide additional computational efficiencies for the data path combined receive beamformer disclosed in Magee '375 by reducing cycle count per block of beamformed data which allows more blocks of beamformed data to be processed per computing device (e.g., DSP, FPGA or ASIC), and also allows more scanlines to be processed per computing device.

Figure 2:
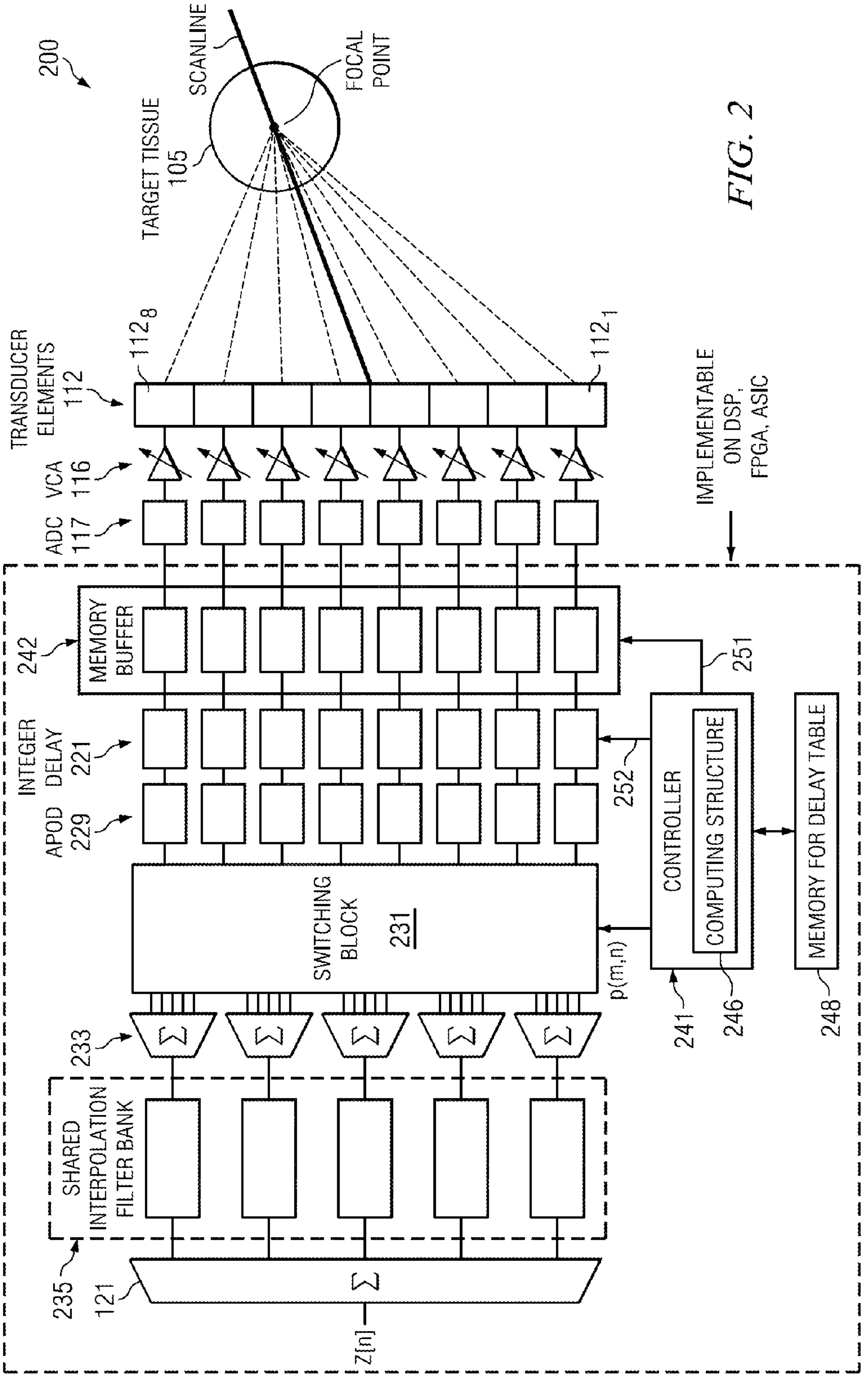
FIG. 2 is a simplified block diagram depiction of a delay and sum, data path combined ultrasound receive beamformer system having a shared interpolation filter bank and control signal generating data architecture implementing fractional delay value sorting for imaging target tissue, according to an embodiment of the invention.

FIG. 2 shows simplified block diagram depiction of a delay and sum, data path combined ultrasound receive beamformer system 200 having a shared interpolation filter bank and control signal generating data architecture implementing delay value sorting for imaging a target tissue 105, according to an embodiment of the invention. Beamformer system 200 comprises a transducer array 112 comprising a plurality (M) of transducer elements shown as elements $112_1$-$112_8$ that each define data channels which comprise piezoelectric transducers that convert sound waves echoed by the target tissue 105 into electrical sensing signals. Transducer elements $112_1$-$112_8$ thus form the first element in the separate data channels 1 through 8 (one per transducer element) that extend from the transducer elements 112$_1$-112$_8$ to apodization blocks 229 as described below.

As in conventional delay and sum ultrasound receive beamformer system 100 shown in FIG. 1, the respective transducers in transducer array 112 are each coupled to a VCA 116 then to an ADC 117 for digital conversion of the amplified transducer signal. The ADCs 117 in FIG. 2 are coupled to memory buffers 242 which stores the digitized and voltage translated sensing signals provided by the respective data channels 1 through 8 in system 200. The outputs of memory buffers 242 are each coupled to integer delays 221, which provide appropriate integer delays to compensate for different echo arrival times due to path length differences between the target tissue 105 and the respective transducer elements 112$_1$-112$_8$. The integer delays 221 are coupled to apodization gain blocks 229 for scaling (i.e. weighting) the respective signals provided. Apodization gains provided by the apodization gain blocks 229 can generally be changed on a sample-by-sample basis.

The outputs of the respective apodization gain blocks 229 are coupled to a switching block 231. Switching block 231 controls which of the P interpolation filters in shared interpolation filter bank 235 (one interpolation filter providing a delay $h_0$, a second interpolation filter providing a delay $h_1$, . . . ) to direct respective channel data received from the apodization gain blocks 229 to, based on the control information provided by the control signal p(m,n) shown in FIG. 2.

Significantly, the interpolation filters in shared interpolation filter bank 235 are not dedicated to process channel data from data channels 1 to 8 originating from a particular one of the transducer elements 112$_1$-112$_8$, in contrast to each of the P interpolation filters in each of the interpolation filter banks 119 in conventional delay and sum ultrasound receive beamformer system 100 shown in FIG. 1. As described above this feature allows the minimum number of interpolation filters for a given ultrasound receive beamformer system implementation to be determined using the desired timing resolution Tres, such that that total number of interpolation filters in the beamformer system 200=P=ceil(Ts/Tres).

A plurality of pre-summing blocks 233 are shown interposed between switching block 231 and the shared interpolation filter bank 235. Switching block 231 is operable to generally direct signals from any of the data channels 1 to 8 in the system 200 to any of the pre-summing blocks 233 for processing by a given one of the P interpolation filters in shared interpolation filter bank 235. Although four (4) signals are shown output by switching block 231 to each of the pre-summing blocks 233, embodiments of the invention can couple less than four (4) signals or as many signals as the number of transducer elements 112/number of data channels. An adder 121 sums the P signals from the P interpolation filters in the shared interpolation filter bank 235 to generate the desired beamformed signal z[n] which can then be used to form an image of the target tissue 105 on a suitable display device.

For the data path combined ultrasound receive beamformer system 200 the Inventor has recognized there are different ways to direct the beamformed data associated with the respective data channels output by their respective apodization blocks 229 to the appropriate one of the P interpolation filters in shared interpolation filter bank 235. As described above, each of the P interpolation filters in shared interpolation filter bank 235 can provide a different fractional delay value.

System 200 includes a controller 241 that comprises a computing structure 246. Controller 241 can be provided by devices including one or more DSPs, FPGAs or ASICs. For example, a DSP can provide all components of system 200 from memory buffers 242 to adder 121 shown by the dashed line in FIG. 2. System 200 includes memory 248 for storing channel data including channel delay data that is coupled to controller 241. Controller 241 is operable to load channel delay data from memory 248 for processing and store processed channel delay data in memory 248.

To compute the total amount of delay time (i.e., both integer and fractional) it takes for a sound wave to propagate from the current focal point and scan line of the target tissue 105 to the $i^{th}$ transducer element in the transducer array, as known in the art, the delay time $\tau_i[n]$, can be represented in terms of discrete-time samples by multiplying by the sampling rate of the beamforming system, $f_s$, as follows $$\tau_i[n] = \frac{f_s}{c}\sqrt{(R_{fp}[n]\sin(\theta) - (x_i - x_c))^2 + (R_{fp}[n]\cos(\theta))^2}$$

where c is the speed of sound for the material/medium, and θ is the angle between the scanline and a reference axis. Controller 241 can calculate the total delay time (integer delay and fractional delay), such as using the equation above. Delay time data calculated by computing structure 246 of controller 241 is stored in memory 248.

Controller 241 is also shown in FIG. 2 providing control signals to both memory buffers 242 and integer delay blocks 221. The control signals 251 to memory buffers 242 provides a time synchronization function which relates the transmit and receive times by denoting a sample start time. The control signals 252 coupled to integer delay blocks 221 implements the calculated integer delay value for the respective data channels at each time instant (n).

Controller 241 also generates control signals p(m,n) which are coupled to switching block 231 that together with pre-summing blocks 233 implements selection of the appropriate one of the P interpolation filters (based on its fractional delay) in shared interpolation filter bank 235 for the desired beamforming (i.e., focal point and scan line) for each of the data channels. As described above, this data structure allows groups of different data channels having the same factional delay value at a particular sample instant (n) to be directed to the particular interpolation filter in shared interpolation filter bank 235 that provides the needed fractional delay value. Thus, control signals p(m,n) are based on the fractional delay values for the channel data obtained from memory 248 at each sample number (n), and are operable to select the appropriate one of the P interpolation filters in shared interpolation filter bank 235 that the particular channel data output by the respective apodization blocks 229 is coupled to.

The pre-summing blocks 233 are each shown having four (4) exemplary inputs, such as for a particular example at a time corresponding to sample number (n) data from data channels 1, 3, 5 and 8 to the top one of the presumming blocks 233 to direct the channel data associated with data channels 1, 3, 5 and 8 to the top one of the P interpolation filters in shared interpolation filter bank 235. In one particular embodiment, the top one of the P interpolation filters in shared interpolation filter bank 235 provides no fractional delay.

A first data summing option is to use the integer delay values and the fractional delay values stored in memory 248 that are a function of sample number (n) and channel number (m). In a software implementation of this option, controller 241 provides two separate loops that index (i.e. search) over the sample number (n) and channel number (m), respectively, that is stored in memory 248, and accumulates the delay data inputs in memory 248 for each of the P filters in shared interpolation filter band 235. A limitation for this approach is that a load must occur from memory 248 to controller 241 and a store must occur from controller 241 to memory 248 as a function of sample number (n) for every data channel (m) to properly accumulate the data for each filter input because the required interpolation filter number (i.e. with its associated fractional delay) in shared interpolation filter bank 235 varies from data channel to data channel. As a result, the memory accesses can become a bottleneck in this option/implementation.

A second data summing option is to sort the integer delay and fractional delay values for the channel data in memory 248 into a sorted table format that now contains the channel number (m), in addition to the integer delay and fractional delay values provided in the first data summing option as a function of sample number (n) and channel number (m). The channel data is sorted in the sorted table according to its fractional delay value that corresponds to a particular interpolation filter in the shared interpolation filter bank 235 that provides that fractional delay value. As a result, all of the receive data channels (m) needed for each of the P filters in the shared interpolation filter bank 235 are grouped together in the sorted table stored in memory 248.

In a software implementation for the second (sorted) data summing option, controller 241 provides a single loop that indexes the delay table stored in memory 248 over the channel number (m). A benefit of this approach is that only a load must occur from memory 248 for each channel value (m), so unlike the first data summing option described above, there is no need for two (2) loops, one loop over each channel value (m) and another loop for each sample (n). Instead, the single loop run by controller 241 continues to accumulate the channel data inputs for a given interpolation filter in shared interpolation filter bank 235 until all of the input values for that particular interpolation filter have been read. Only then does the loop run by controller 241 actually filter the accumulated input data. The loop continues until all of the channel delay data has been accumulated in their respective interpolation filter's input.

Figure 3A:
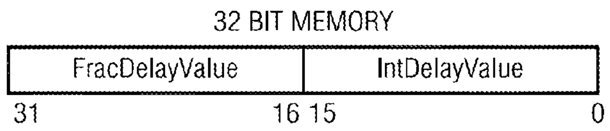
FIG. 3A shows an exemplary channel data format for a 32 bit data channel for a first data summing option, wherein the channel data includes a fractional delay and an integer delay value, according to a disclosed embodiment.

FIG. 3A shows the delay data format for an exemplary 32 bit data channel data for the first data summing option described above. 16 bits are shown representing the fracDelayValue while the remaining 16 bits are shown representing the IntDelayValue.

Figure 3B:
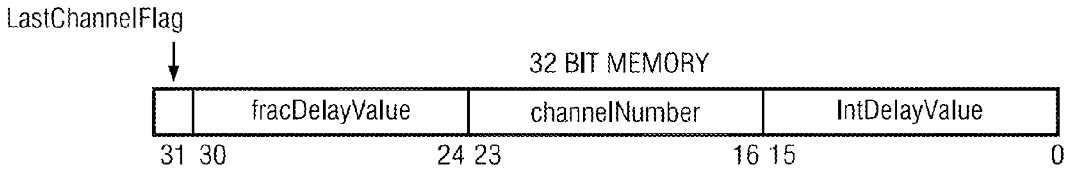
FIG. 3B shows an exemplary channel data format for a 32 bit data channel for a second data summing option, wherein the channel data includes a fractional delay value, the channel number, and an integer delay value, according to a disclosed embodiment.

FIG. 3B shows the delay data format for an exemplary 32 bit data channel data for the second data summing option described above, according to a disclosed embodiment. The delay data format for the second option includes the channel number, integer delay and fractional delay values. There is a channel number field provided since after sorting based on the fractional delay value, the channel data will not be consecutive from low to high data channels in the resulting delay table as it will be for the unsorted alternative described above relative to the first data summing option (FIG. 3A). The last channel flag bit (bit 31) is only set in the delay value table for the last input data channel for a given one of the P interpolation filters in shared interpolation filter band 235. This aspect is described below with respect to FIG. 3C.

FIG. 3C is an exemplary delay value table that shows channel data including channel number (m), fractional delay, and integer delay, the channel data shown in both an unsorted table in a hexadecimal (hereafter "Hex") representation, and a sorted table in a Hex representation, at a particular sample time (n) for channel data from an exemplary 16 channel system, according to a disclosed embodiment. The unsorted table format is based on the channel data format shown in FIG. 3A, while the sorted table format is based on the channel data format shown in FIG. 3B, which can be considered to be a re-mapping of the channel data in the unsorted delay table. The arrows shown show the mapping of data channels 3, 7, 8 and 12 (which all have a fractional delay value of 0) into the first, second, third and fourth positions in the sorted table. As known in the art, each hexadecimal character represents 4 binary bits. The leftmost characters "0x" in the unsorted table format and sorted table format simply indicates that the data values are represented in Hex format.

In the unsorted table shown, the rightmost 4 Hex characters represent the integer delay while the next 4 Hex characters represent the fractional delay. The fractional delay values can be seen to be changing between the values of 0, 1, 2 and 3 between each and every of the 16 rows (data channels).

In the sorted table shown, the rightmost 4 Hex characters represent the integer delay, the fifth and sixth Hex characters represents the channel number, the seventh Hex character represents the lower portion of the fractional delay, with the eight Hex character representing the upper portion of the fractional delay value and the last channel flag ($8^{th}$ bit in the eighth Hex character when the flag is set). In contrast to the unsorted table format, in the sorted table format it can be seen that channel numbers 3, 7, 8 and 12 which all have a fractional delay value of 0 can be seen to be in the first (i.e. topmost), second, third and fourth (row) entries in the sorted table, then the data channels 2, 6, 9 and 13 that have a fractional delay value of 1, then the data channels 1, 5, 10 and 14 that have a fractional delay value of 2, and finally the channels 0, 4, 11 and 15 that have a fractional delay value of 3. The last channel flag can be seen to correspond to the fourth (i.e. the last) data channel for each of the fractional delay groupings, such as channel 12 for fractional delay of 0. This sorted table structure thus groups together the data channels to be summed and applied as inputs for each of the P interpolation filters in the shared interpolation filter bank 235 for the beamformer system 200. Since loads from memory 248 to controller 241 only occur once for each fractional delay value (corresponding to a particular one of the P interpolation filters in the shared interpolation filter bank 235), the sorted data structure shown significantly reduces the number of loads from memory 248.

For the example shown in FIG. 3C, the unsorted table structure involves 64 loads from memory 248 per sample instant (n) corresponding to the number of transducers/data channels. Significantly, the sorted table structure involves only 16 loads from memory 248 corresponding to the number of interpolation filter P in the shared interpolation filter bank 235 for each sample instant.

Figure 4:
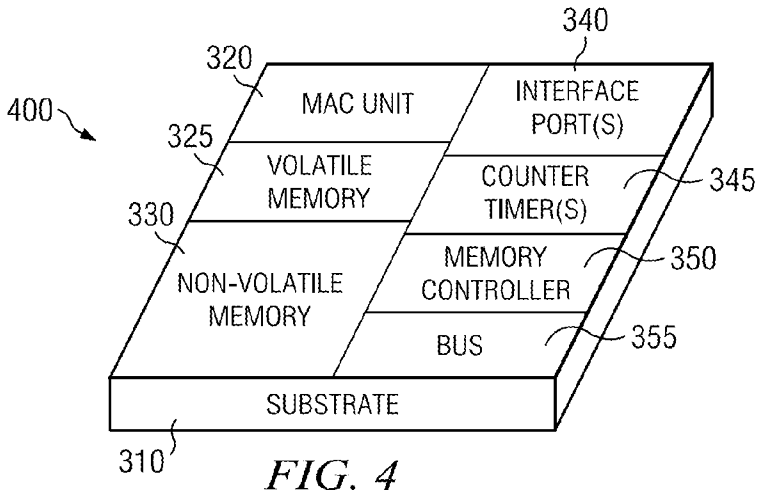
FIG. 4 shows a simplified block diagram of a DSP IC according to an embodiment of the invention that can implement all the system elements within the dashed line shown in FIG. 2.

FIG. 4 shows a simplified block diagram of a DSP IC 400 according to an embodiment of the invention that can implement all the system elements within the dashed line shown in FIG. 2. These components comprise memory buffers 242, integer delays 221, apodization gain blocks 229, switching block 231, pre-summing blocks 233, shared interpolation filter bank 235, adder 121, as well as memory 248 for delay table and controller 241 for generating the control signal p(m,n) that is applied to switching block 231 for directing the channel data to any of the P interpolation filter in shared interpolation filter bank 235.

DSP IC 400 is shown formed on a substrate 310 having a semiconductor surface (e.g., a silicon substrate) and comprises a multiply-accumulate (MAC) unit 320 that is operable to generate control signals, such as p(m,n) shown in FIG. 2. DSP IC 400 generally includes a volatile memory (e.g., RAM) 325 and non-volatile memory (e.g., ROM) 330. Algorithms according to embodiments of the invention can be stored in non-volatile memory 330. The DSP IC 400 is also shown including interface port(s) 340 for inputs and outputs, counter/timers 345, memory controller 350 and bus 355.

As with conventional DSPs, the DSP IC 400 can execute instructions to implement one or more digital signal processing algorithms or processes. For instance, the instructions data can include various coefficients and instructions that, when loaded and initialized into DSP IC 400, can prompt the DSP IC 400 to implement different digital signal processing algorithms or processes, such as a digital filter. The DSP IC 400 can receive data from ADC's 117 shown in FIG. 2 and then apply algorithms to the data according to its current configuration.

MAC unit 320 generally includes delaying and apodizing circuitry for processing digitized ultrasound sensing signals to form delayed and apodized digital ultrasound sensing signals. MAC unit 320 also generally includes data path combining circuitry for generating data combinations of the plurality of delayed and apodized digital sensing signals to include two or more delayed and apodized digital sensing signals that originate from different transducer elements.

MAC unit can also provide the controller 241 and computing structure. Volatile memory 325 can provide the memory for the delay table.

Moreover, MAC unit 320 generally provides the shared interpolation filter bank that is coupled to the output of the data path combining circuitry 233 in FIG. 2 for interpolation filtering the data combinations to generate a second plurality of delayed and apodized digital sensing signals. As described above, the second plurality of delayed and apodized digital sensing signals output by the shared interpolation filter bank 235 in FIG. 2 are combined by an adder 121 in FIG. 2 to generate the ultrasound receive beamformed signal. MAC unit 320 can also generally provide the adder 121.

Figure 5:
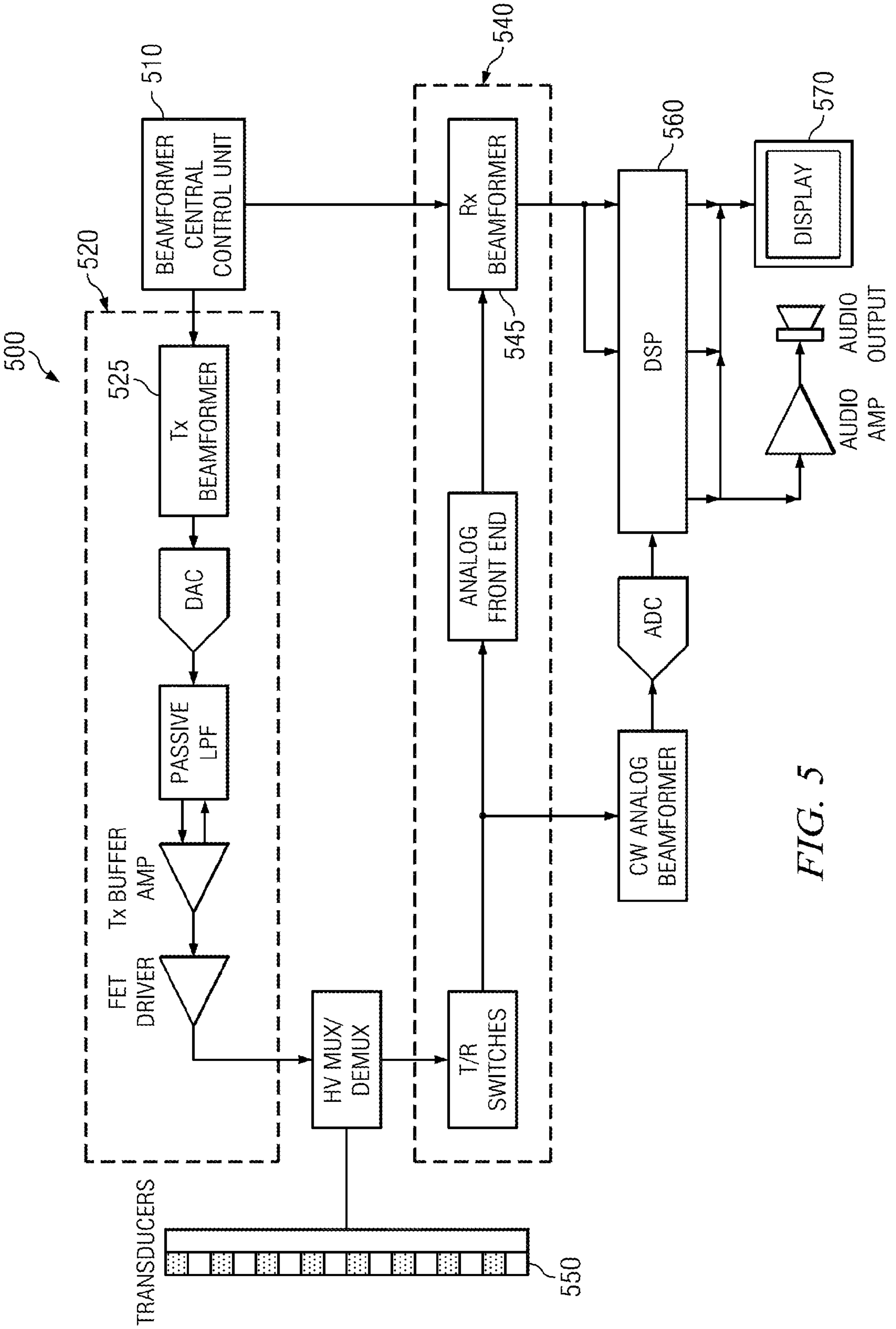
FIG. 5 is a block diagram of an exemplary ultrasound system that can implement data path combined ultrasound receive beamformer system having control signal generating data architecture implementing delay value sorting, according to a disclosed embodiment.

FIG. 5 is a block diagram of an exemplary ultrasound system 500 that can implement data path combined ultrasound receive beamformer system 200 having control signal generating data architecture implementing delay value sorting, according to a disclosed embodiment. System 500 includes a transmit section 520 comprising transmit (Tx) beamformer 525 and a receive section 540 comprising receive (Rx) beamformer 545 that share a common array of transducers 550.

System 500 includes a beamformer central control unit 510 that is coupled to both Tx beamformer 525 and Rx beamformer 545. Beamformer central control unit 510 can be embodied as a DSP, such as DSP IC 400 described above relative to FIG. 4, for implementing the data path combined ultrasound receive beamformer system 200 having control signal generating data architecture implementing delay value sorting shown in FIG. 2. Rx beamformer 545 of receive section 540 is coupled to a backend imaging DSP 560. Backend imaging DSP 560 is coupled to a display 570.

Figure 6:
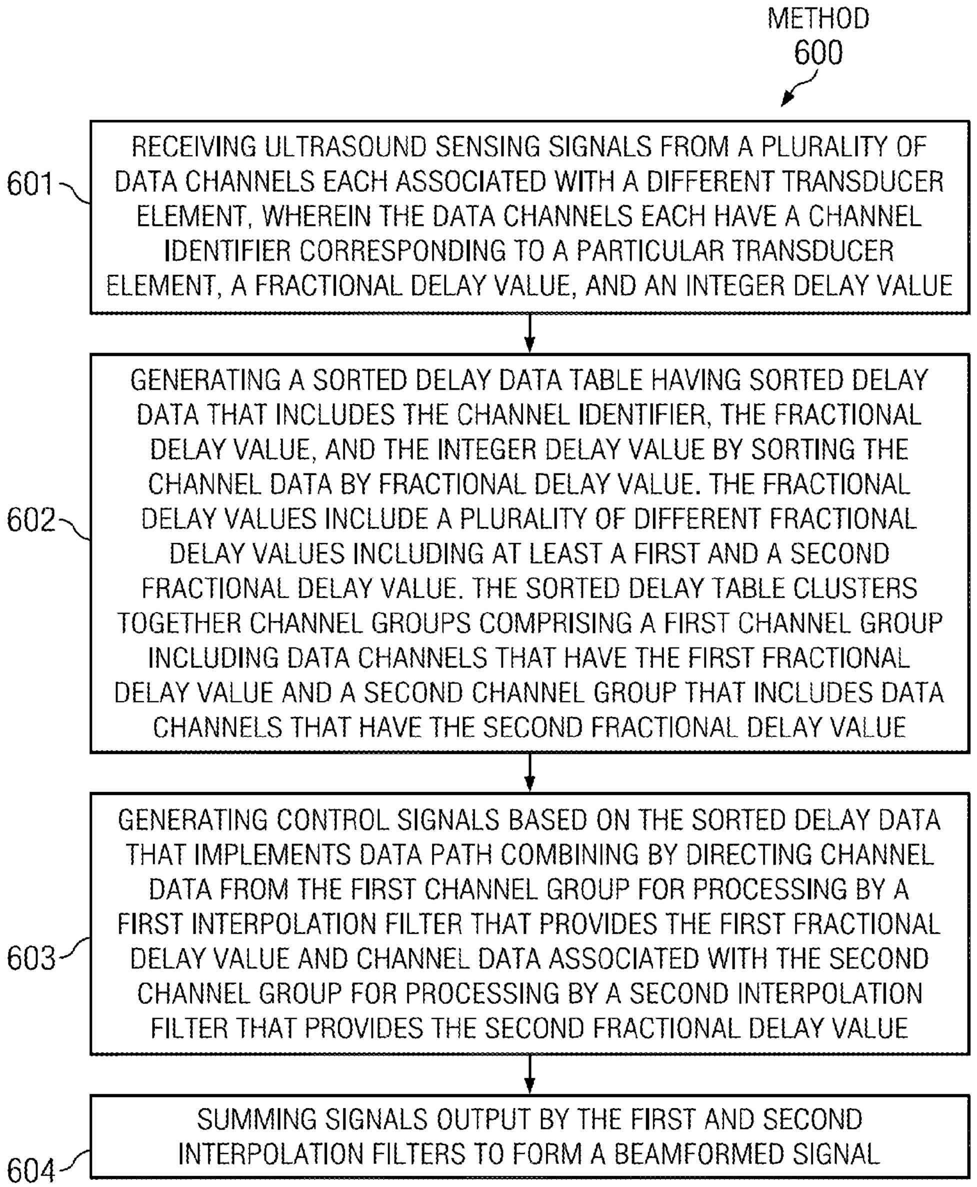
FIG. 6 is a flow chart for an exemplary method of ultrasound receive beamforming that includes delay value sorting, according to an embodiment of the invention.

FIG. 6 is a flow chart for an exemplary method 600 of ultrasound receive beamforming that includes delay value sorting, according to an embodiment of the invention. Step 601 comprises receiving ultrasound sensing signals from a plurality of data channels each associated with a different transducer element, wherein the data channels each have a channel identifier (e.g., channel number) corresponding to a particular transducer element, a fractional delay value, and an integer delay value. In step 602, a sorted delay data table is generated for the plurality of data channels that comprises sorted delay table data that includes the channel identifier, the fractional delay value, and the integer delay value. The fractional delay values include a plurality of different fractional delay values including at least a first and a second fractional delay value. The sorted delay table data clusters together channel groups comprising a first channel group including data channels that have the first fractional delay value and a second channel group that includes data channels that have the second fractional delay value.

Control signals are generated in step 603 based on the sorted delay table data that implements data path combining by directing channel data from the first channel group for processing by a first interpolation filter that provides the first fractional delay value and channel data associated with the second channel group for processing by a second interpolation filter that provides the second fractional delay value. Step 604 comprises summing signals output by the first and second interpolation filters to form a beamformed signal. The interpolation filters are generally in a single shared interpolation filter bank, wherein the plurality of interpolation filters in the shared interpolation filter bank can each provide different fractional delays.

As described above, disclosed sorted delay data table embodiments permit input values for a given interpolation filter in the shared interpolation filter bank to be accumulated sequentially on the channel count because they are grouped together in the sorted delay value table. Accordingly, the accumulated value is only stored once per interpolation filter and sample count. Benefits of disclosed embodiments based on the sorted delay data table format include improved cycle count performance per block of beamformed data, allowing more blocks of beamformed data to be processed per DSP or other computing structure, and allowing more scanlines to be processed per DSP or other computing structure.

Although generally described for beamforming of sound waves, specifically for ultrasound beamforming applications, embodiments of the invention can also be used for electromagnetic (e.g. RF) applications, such as for radar, wireless communications and radio astronomy. Moreover, embodiments of the invention can be applied to other sound wave processing application, such as for seismology, sonar, and speech.

EXAMPLES

Embodiments of the invention are further illustrated by the following specific examples, which should not be construed as limiting the scope or content of embodiments of the invention in any way.

Cycle Count Comparison for a DSP Using a Sorted Delay Data Table Vs. An Unsorted Delay Data Table The advantage of using a sorted table format based on fractional delay values as disclosed herein for a data path combined ultrasound receive beamformer system such as shown in FIG. 2 can be seen in the cycle count numbers shown in Table 1 below. In Table 1, K is the number of interpolation filter coefficients (per interpolation filter), M is the number of receive data channels (equal to the number of transducers), N is the number of output samples per iteration of the beamformer, and P is the number of interpolation filters in the shared interpolation filter bank 235. The "Integer/Frac table" corresponds to the unsorted table format shown in FIG. 3C, while the "Sorted table" corresponds to the sorted table format also shown in FIG. 3C.

TABLE 1

| Cycle Count Comparisons | | |
|---|---|---|
| | Scan Object | |
| Option | Cyst K = 8; M = 64; N = 128; P = 10 | Kidney K = 8; M = 128; N = 128; P = 10 |
| Integer/Frac Table | 257,846 | 503,606 |
| Sorted Table | 89,423 | 163,151 |

The cycle count improvement for the sorted table format is roughly 65% over the unsorted table format, making the sorted table format disclosed herein advantageous for DSPs, FPGAs and other computational implementations for receive beamforming.

While various embodiments of the invention have been described above, it should be understood that they have been presented by way of example only, and not limitation. Numerous changes to the disclosed embodiments can be made in accordance with the disclosure herein without departing from the spirit or scope of the invention. Thus, the breadth and scope of embodiments of the invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such a feature may be combined with one or more other features of the other implementations as may be desired and advantageous for any given or particular application.

The terminology used herein is for the purpose of describing particular embodiments only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention claimed is:

1. A method of processing ultrasound signals received from a plurality of data channels each associated with different transducer elements, said data channels each having a channel identifier corresponding to a particular one of said transducer elements, a fractional delay value of each channel, and an integer delay value, comprising:

generating a sorted delay data table having sorted delay data by sorting delay data that includes said channel identifier, said fractional delay value, and said integer delay value, wherein said fractional delay value includes a plurality of different fractional delay values including at least a first and a second fractional delay value, said sorted delay table data clustering together channel groups comprising a first channel group including said data channels that have said first fractional delay value and a second channel group that includes said data channels that have said second fractional delay value;

generating control signals based on the sorted delay data that implements data path combining by directing channel data from said first channel group for processing the control signals by a first interpolation filter that provides said first fractional delay value and channel data associated with said second channel group for processing by a second interpolation filter that provides said second fractional delay value, and summing signals output by said first and said second interpolation filter to form a beamformed signal, wherein said plurality of different fractional delay values are given by integer*Tres, wherein Tres is a timing resolution (Tres) for said ultrasound receive beamformed signal and said integer corresponds to integer values from zero to ceil(Ts/Tres)−1, where Ts is a sampling period for digitizing said channel data, wherein ceil (Ts/Tres) is a determination of the greater of Ts or Tres, wherein said beamformed signal at a time sample n for a scan line is calculated using:

$$z[n] = \sum_{k=-\infty}^{\infty} \sum_{m=0}^{M-1} a_m[n] h_{p(m,n)}[k] x_m[n-k-d_m[n]]$$

Wherein:

$p(m, n) \in \{0, 1 \ldots, P-1\}$ $P = \text{ceil}(T_s/T_{res})$ m is a summation over said different transducer elements;

k is a summation over a number of interpolation filter coefficients for said first and said second interpolation filter;

$a_m[n]$ is an apodization factor applied to said channel data associated with an mth data channel at said time sample n;

$x_m[n]$ is a sensing signal generated by an $m^{th}$ element of said different transducer elements at said time sample n, $h_{p(m,n)}[k]$ is the kth coefficient of a $p(m,n)^{th}$ filter of said first and said second interpolation filter at said time sample n, and $d_m[n]$ is an integer delay for said channel data associated with said $m^{th}$ data channel at said time sample n.

2. The method of claim 1, wherein said first interpolation filter and said second interpolation filter are part of a single shared interpolation filter bank consisting of said first interpolation filter, said second interpolation filter, and a plurality of other interpolation filters, and wherein said plurality of other interpolation filters each provide a fractional delay value different from one another and different from said first and said second fractional delay value.

3. The method of claim 1, wherein said different transducer elements comprise piezoelectric transducers.

4. The method of claim 1, wherein said generating said sorted delay data table, said generating said control signals, said interpolation filtering and said summing are performed by at least one digital signal processor (DSP) integrated circuit (IC).

5. An ultrasound diagnostic imaging system, comprising:

a plurality of transducer elements for transmitting ultrasound transmit pulses toward a target tissue region, and receiving echo signals from said target tissue region in response to said transmit pulses;

a transmit section for driving said plurality of transducer elements for said transmitting of said ultrasound transmit pulses, and a receive section for processing a plurality of sensing signals generated by said plurality of transducers responsive to said echo signals, said receive section defining a plurality of data channels each associated with different one of said plurality of transducer elements, said receive section comprising:

digitizing blocks, integer delaying blocks and apodizing blocks for processing said sensing signals in each of said plurality of data channels;

data path combining circuitry for generating a plurality of data combinations by combining channel data from two or more of said plurality of data channels, said channel data including a channel identifier, a fractional delay value, and an integer delay value;

a shared interpolation filter bank comprising a plurality of interpolation filters comprising a first interpolation filter that provides a first fractional delay value and a second interpolation filter that provides a second fractional delay value coupled to an output of said data path combining circuitry for interpolation filtering said plurality of data combinations;

a controller and associated memory, wherein said controller (i) generates a sorted delay data table having sorted delay data by sorting said channel data, said sorted delay data table clustering together channel groups so that a first channel group includes said data channels that have said first fractional delay value and a second channel group that includes said data channels that have said second fractional delay value, and (ii) generates control signals based on said sorted delay data that are coupled to said data path combining circuitry for by directing said channel data from said first channel group for processing by said first interpolation filter and said channel data associated with said second channel group for processing by said second interpolation filter;

a summer for summing coupled to outputs of said single shared interpolation filter bank to form a beamformed signal;

a backend imaging display processor coupled to receive and process said beamformed signal to generate a display signal, said display signal being suitable for causing display devices to produce an image, and a display device for receiving said display signal and producing said image, wherein said data combinations are selected from the group consisting of:

only Channel ID;

fractional delay values; and integer delay values, wherein said plurality of interpolation filters each provide a different one of said fractional delay values wherein said different fractional delay values are based on integer*Tres, wherein Tres is a timing resolution (Tres) for said beamformed signal and said integer corresponds to integer values from zero to ceil(Ts/Tres)−1, where Ts is a sampling period for said digitizing, wherein ceil (Ts/Tres) is a determination of the greater of Ts or Tres, wherein said beamformed signal at a time sample n for a scan line is calculated using:

$$z[n] = \sum_{k=-\infty}^{\infty} \sum_{m=0}^{M-1} a_m[n] h_{p(m,n)}[k] x_m[n-k-d_m[n]]$$

wherein:

$p(m, n) \in \{0, 1 \ldots, P-1\}$ $P = \mathrm{ceil}(T_s/T_{res})$ m is a summation over said plurality of transducer elements;

k is a summation over a number of interpolation filter coefficients for said plurality of interpolation filters;

$a_m[n]$ is an apodization factor applied by one of said apodizing blocks for an $m^{th}$ channel of said data channels at said time sample n, $X_m[n]$ is said sensing signal generated by an $m^{th}$ element of said plurality of transducer elements at said time sample n, $h_{p(m,n)}[k]$ is the $k^{th}$ coefficient of the $p(m,n)^{th}$ filter of said plurality of interpolation filters at said time sample n, and $d_m$[nJ is an integer delay for said channel data associated with said mth of said plurality of transducer elements at said time sample n.

6. The system of claim 5, wherein said data path combining circuitry is implemented by a switching circuit that receives said control signals.

7. The system of claim 5, wherein at least one digital signal processor (DSP) integrated circuit ("IC") provides said integer delaying, said apodizing blocks, said data path combining circuitry, said shared interpolation filter bank, said controller and associated memory, and said summer.

8. A digital signal processor (DSP) integrated circuit (IC) for ultrasound signal processing, comprising:

a substrate having a semiconductor surface;

integer delaying blocks and apodizing blocks for processing sensing signals in each of a plurality of data channels;

data path combining circuitry for generating a plurality of data combinations by combining channel data from two or more of said plurality of data channels, said channel data including a channel identifier, a fractional delay value, and an integer delay value;

a shared interpolation filter bank comprising a plurality of interpolation filters comprising a first interpolation filter that provides a first fractional delay value and a second interpolation filter that provides a second fractional delay value coupled to an output of said data path combining circuitry for interpolation filtering said plurality of data combinations;

a controller and associated memory, wherein said controller (i) generates a sorted delay data table having sorted delay data by sorting said channel data, said sorted delay data table clustering together channel groups so that a first channel group includes said data channels that have said first fractional delay value and a second channel group that includes said data channels that have said second fractional delay value, and (ii) generates control signals based on said sorted delay data that are coupled to said data path combining circuitry for by directing said channel data from said first channel group for processing by said first interpolation filter and said channel data associated with said second channel group for processing by said second interpolation filter, and a summer for summing coupled to outputs of said single shared interpolation filter bank to form a beamformed signal wherein said different fractional delay values are based on integer*Tres, wherein Tres is a timing resolution (Tres) for said beamformed signal and said integer corresponds to integer values from zero to ceil(Ts/Tres)−1, where Ts is a sampling period for digitizing, wherein ceil (Ts/Tres) is a determination of the greater of Ts or Tres, wherein said beamformed signal at a time sample n for a scan line is calculated using:

$$z[n] = \sum_{k=-\infty}^{\infty} \sum_{m=0}^{M-1} a_m[n] h_{p(m,n)}[k] x_m[n-k-d_m[n]]$$

Wherein:

$p(m, n) \in \{0, 1 \ldots, P-1\}$ $P = \text{ceil}(T_s/T_{res})$ m is a summation over said plurality of transducer elements;

k is a summation over a number of interpolation filter coefficients for said plurality of interpolation filters;

$a_m[n]$ is an apodization factor applied of said apodizing blocks for an mth channel of said data channels at said time sample n;

$X_m[n]$ is said sensing signal generated by an mth element of said plurality of transducer elements at said time sample n;

$h_{p(m,n)}[k]$ is the kth coefficient of the p(m,n)th filter of said plurality of interpolation filters at said time sample n, and $d_m[n]$ is an integer delay for said channel data associated with said mth of said plurality of transducer elements at said time sample n.

9. The DSP IC of claim 8, wherein said plurality of interpolation filters each provide a different one of said fractional delay values.

10. The DSP IC of claim 8, wherein said data path combining circuitry is implemented by a switching circuit that receives said control signals.

* * * * *